(12) United States Patent
Han et al.

(10) Patent No.: US 9,180,153 B2
(45) Date of Patent: Nov. 10, 2015

(54) SOPHORAE RADIX EXTRACT FOR PREVENTION AND TREATMENT OF RESPIRATORY DISEASES

(75) Inventors: Chang-Kyun Han, Seoul (KR); Kiwon Joung, Anyang-si (KR); Hunseung Yoo, Seoul (KR); Yong-Baik Cho, Anyang-si (KR); Keun Ho Ryu, Seoul (KR); Hye Yeon Baek, Seoul (KR); Taek-Soo Kim, Suwon-si (KR); In Ho Jung, Suwon-si (KR); Wie-Jong Kwak, Seoul (KR)

(73) Assignee: SK Chemicals Co., Ltd., Gyeonggi-Do (KR)

( * ) Notice: Subject to any disclaimer, the term of this patent is extended or adjusted under 35 U.S.C. 154(b) by 0 days.

(21) Appl. No.: 12/778,793

(22) Filed: May 12, 2010

(65) Prior Publication Data

US 2010/0221371 A1    Sep. 2, 2010

Related U.S. Application Data

(63) Continuation of application No. 11/666,392, filed as application No. PCT/KR2005/003522 on Oct. 21, 2005, now abandoned.

(30) Foreign Application Priority Data

Oct. 27, 2004    (KR) ......................... 10-2004-0086282

(51) Int. Cl.
*A61K 36/489*    (2006.01)

(52) U.S. Cl.
CPC ........... *A61K 36/489* (2013.01); *A61K 2236/33* (2013.01)

(58) Field of Classification Search
None
See application file for complete search history.

(56) References Cited

U.S. PATENT DOCUMENTS 5,997,877 A  *  12/1999  Chang .......................... 424/757
2003/0190375 A1 *  10/2003  Erdelmeier et al. .......... 424/725

FOREIGN PATENT DOCUMENTS

| CN | 1101278 | 4/1995 |
|---|---|---|
| JP | 04-346912 | 12/1992 |
| KR | 1999-0073578 | 10/1999 |
| KR | 10-2001-0001582 | 1/2001 |
| KR | 2003039509 | 5/2003 |
| KR | 10-2004-0022763 | 3/2004 |

OTHER PUBLICATIONS

Huang et al. The Pharmacology of Chinese Herbs. CRC Press. 1999. pp. 399-400.*
Brossi. The Alkaloids: Chemistry and Pharmacology. Academic Press. 1991. pp. 35-36.*
Extract. Retrieved from the internet. <http://en.wikipedia.org/wiki/Extract>. Retrieved on Jul. 6, 2011. 1 page.*
Lee et al. (2000) Kor. J. Pharmacogn. 31(3): 273-279.*
Website document entitled: "Lower Repiratory Tract Infection" (available at http://en.wikipedia.org/wiki/Lower-Respiratory_Tract_Infection). Archived to Jan. 31, 2005.*
Website document entitled: "Upper Respiratory Tract Infection" (available at http://en.wikipedia.org/wiki/Upper_Respiratory-Tract_Infection). Achived to Oct. 24, 2004.*
Balter et al. (1997) Inter. J. Antimicrobial Agents 9, 83-93.*
Korbila et al. (2009) Canadian Family Physician vol. 55, 60-67.*
Olszewska et al. (2009) Expert Opin. Emerging Drugs 14(2), 207-217.*
Reichmuth et al. (2000) BioDrugs 14(6), 371-387.*
Cy, Chuang et al.: "Ocular anti-inflammatory actions of matrine", *J.Ocul.Pharmacol*, 1987 Summer;3(2): retrieved from internet (http://www.ncbi.nlm.nih.gov/entrez/query).
Cho, C.H. et al.: "Study of the Antipyretic Activity of Matrine A Lupin Alkaloid Isolated from *Sophora subprostrata*", Planta Med. *1986*: (5): pp. 343-345.
Chuang, C.Y.; Xiao, J.G.; Chiou, G.C.Y.: "Ocular Anti-Inflammatory Actions of Matrine", *Journal of Ocular Pharmacology*, vol. 3, No. 2, 1987, pp. 129-134.
Baiter et al. Management of Chronic Bronchitis and Acute Exacerbations of Chronic Bronchitis. International Journal of Antimicrobial Agents 9. (1997) 83-93.
Reichmuth et al. Present and Potential Therapy for Allergic Rhinitis. BioDrugs. 2000. Dec. 14, Abstract.
Regal JF. Immunologic Effector Mechanisms in Animal Models of Occupational Asthma. J. Immunotoxicol. Jan. 1, 2004(1) Abstract.
Ho-Sub. Anti-Allergic Activity of the Sophorae Radix Water Extract in Experimental Animals. American Journal of Chinese Medicine. Winter 2001. pp. 1-3.
Korbila et al. Penicillins vs. Trimethoprim-Based Regimens for Acute Bacterial Exacerbations of Chronic Bronchitis. Canadian Family Physician. vol. 55 Jan. 2009. pp. 60-67.
Olszewska et al. Emerging Drugs for Respiratory Syncytial Virus Infection. Expert Opin Emerg Drugs. Jun. 2009. 12(2). pp. 1-19.

(Continued)

*Primary Examiner* — Chris R Tate
*Assistant Examiner* — Russell Fiebig
(74) *Attorney, Agent, or Firm* — Frommer Lawrence & Haug LLP (57) ABSTRACT

The present invention relates to an extract isolated from Sophorae Radix useful for prevention and treatment of respiratory diseases. More specifically, the present invention relates to a pharmaceutical drug comprising the Sophorae Radix extract having excellent effects of inhibiting airway contraction, respiratory infections, 5-lipoxygenase activity, phosphodiesterase 4 activity, airway hyper-responsiveness and airway remodeling; antagonistic activity against leukotriene D4; and an antitussive effect, thus being useful for prevention and treatment of respiratory diseases such as asthma, acute or chronic bronchitis, allergic rhinitis, acute upper respiratory infections and acute lower respiratory infections, and the like.

10 Claims, 5 Drawing Sheets

(56) References Cited

OTHER PUBLICATIONS

Lower Respiratory Tract Infection. retrieved from the internet. <http://en.wikipedia.org/wiki/Lower_respiratory_tract_infection>. Retrieved Oct. 1, 2009. pp. 1-5.

Upper Respiratory Tract Infection. retrieved from the internet. <http://en.wikipedia.org/wiki/Upper_respiratory_tract_infection>. Retrieved Oct. 1, 2009. pp. 1-2.

Philipson. New Drugs From Nature—It Could Be Yew. Phytotherapy research. 13. 1999. pp. 2-9.

Revilla. Comparison of Several Procedures Used for Extraction of Anyhocyanins From Red Grapes. J. Agric. Food Chem. 1119. 56. pp. 4592-4597.

Lee, Hwa-Jin et al.: "Screening of Leukotriene $B_4$ Receptor Antagonist Activity from the Herbal Drugs", *Kor. J. Pharmacogn.*, 31(3), 2000, pp. 273-279, in Korean, Includes English Abstract.

Office action issued on Jun. 15, 2010 by Korean Intellectual Patent Office for corresponding application, 6 pages.

\* cited by examiner

SOPHORAE RADIX EXTRACT FOR PREVENTION AND TREATMENT OF RESPIRATORY DISEASES

CROSS REFERENCE TO RELATED APPLICATIONS

This application is a continuation of U.S. patent application Ser. No. 11/666,392 filed Sep. 19, 2007 now abandoned entitled "Sophorae Radix Extract For Prevention And Treatment Of Respiratory Diseases" which is a 371 of PCT/KR2005/003522 filed on Oct. 21, 2005, published on May 4, 2006 under publication number WO 2006/046814 A1 which claims priority benefits from Korean Patent Application No. 10-2004-0086282 filed Oct. 27, 2004, the disclosures of which are incorporated herein by reference.

FIELD OF THE INVENTION

This invention relates to Sophorae Radix extract useful for prevention and treatment of respiratory diseases. This invention also relates to a pharmaceutical drug comprising Sophorae Radix extract useful for prevention and treatment of respiratory diseases due to their excellent effects in preventing airway contraction, respiratory infection, 5-lipoxygenase, phosphodiesterase 4, airway hyper-responsiveness or airway remodeling, leukotriene D4, as well as having an antitussive effect.

BACKGROUND OF THE INVENTION

Asthma is a typical respiratory disease having repetitive and spasmodically symptoms of difficulty in breathing, coughs and stridor. About 30% pediatric asthma patients start to show the symptoms within one year from birth while about 80% of asthma patients show the symptoms at the age of 4-5. In Korea, the rate of asthma outbreak is about 10%.

The incidence rate of asthma varied to some extent depending on the country, race, age and the like. According to the British report in 1991, about 7% of adults and 13.5% of children are suffering from asthma. In Korea, the number of asthma patients is on the increase due to the drastic change in life styles as well as in environmental conditions such as severe pollution and accumulated stress. The age of developing asthma has been lowered recently due to environmental contamination such as pollution and its symptoms have been prolonged.

Respiratory obstruction as one of characteristics of asthma occurs via 3 steps: i.e., contraction of bronchial smooth muscle, tylosis of pulmonary mucosa, and accumulation of sticky mucus in bronchi and bronchioles. Of them, contraction of bronchial smooth muscle is rather easily recovered.

In the attack of extrinsic (allergic) asthma, it is known that IgE plays a very important role and IgG is also often involved. IgE releases mediators (histamine, SRS-A, ECF-A, NCF, PAF, Kinin, PGs, etc.) which induce a hypersensitivity reaction by activating mast cells. The cause of intrinsic (non-allergic) asthma is still not known but this kind of asthma appears to be mediated by autonomic nerves. In an intrinsic asthma patient, a cholinergic stimulus can directly release mediators such as histamine from mast cells, increase secretion of goblet cells, dilate pulmonary blood vessels, and contract trachea, bronchi, and large bronchioles, thereby causing bronchial spasm and increasing release of mucus.

So far there is no cure for asthma. Although there are many methods and drugs which have been used for the prevention of spasm and complications due to asthma they have not been satisfactory. One of the most effective ways of preventing the attack of asthma may be to find the very factors that are involved in causing asthma. Examples of therapeutic agents that have been used to treat asthma are inhaling bronchodilator drugs, oral or injectable bronchodilator drugs (sympathetic stimulators and theophyllines), steroid preparations (inhaling, oral and injectable form, etc.), leukotriene antagonists (montelukast, pranlukast, zileuton, etc.), anti-allergic drugs (cromolyn disodium, ketotifen, etc.) and the like.

Bronchitis can be either acute or chronic. According to its causes, bronchitis is divided into allergic, infectious, and extrinsic bronchitis, while pathologically it is classified catarrhalis, suppurative, occlusive, ulcerative, and infiltrative bronchitis. The most frequent cause of bronchitis is due to infection with bacteria, viruses, fungi and the like. People who normally not infected with the above pathogens can be infected when their systemic immune system gets weakened. Allergic bronchitis can be a direct allergic reaction due to inhalation of allergens or a partial symptom due to a generalized allergic reaction. Extrinsic bronchitis may occur due to a chemical stimulus such as chlorine and sulfur dioxide gas, or due to a physical stimulus such as dusts. People living in large cities with polluted air can be readily exposed to respiratory infections. In case of acute bronchitis, from the pathological point of view, it is easy to observe rubber, swelling, and xerosis and also mucous or suppurative secretions. In general, asthmas can be recovered without incurring complications. However, if it is progressed into a chronic asthma, it results in swelling, tylosis and atrophy. In a prolonged chronic asthma, it results in fiber proliferation, bronchostenosis or pulmonary emphysema. The most peculiar symptoms of bronchitis are coughs and phlegm. If the cause of bronchitis is due to infection, there often develops fever and chest pain, whereas if it is due to extrinsic factors, there often develops irritations on the mucus of mouth, nose, eye, etc. In therapy, cough is considered as a sort of a bodily defense and thus it is not recommended to intentionally stop coughing. It is essential that a therapy for the cause be conducted along with other measures. In winter, it is desirable to increase room temperature and administer a small amount of codeine, atropine, ephedrine, antihistamine agents, and the like. Use of steroids or theophyllines for treating infections is not satisfactory.

Nasal allergic inflammation often refers to nasal allergy or allergic rhinitis. It entails symptoms of sudden continuous coughs, release of a large amount of clear nasal mucus, stuffy nose, heavy head, release of tears, and the like. When the symptoms are similar but the allergens are not identified it is coryza vasomotoria. For example, the above symptoms may occur when body temperature is temporarily lowered in the morning and they are usually recovered within a few hours, and these symptoms are commonly seen in people in a cold season. This can be sometimes confused with nasal cold but it differs from the cold and often accompanies asthma and hives.

The allergic reaction in allergic rhinitis is an antigen-antibody hypersensitivity reaction, wherein histamine is released from mast cells and cell walls of basophils, and arachidonic acid is released to produce prostaglandins and leukotrienes by cyclooxygenase (COX) and 5-lipooxygenase(5-LO), thereby mediating the initial reaction occurring between 2-90 min after being exposed to an antigen and the post reaction occurring 4-8 hrs thereafter. The initial reaction is proceeded with by a mediating substance while the post reaction is mediated by cell infiltration. Further, allergic and non-allergic rhinitis both serve as risk factors for developing asthma.

In therapies, desensitization is performed when the antigen is clearly identified. Other therapies such as use of drugs, surgeries, physical therapies but they are not considered as a complete cure.

There are various respiratory infections due to such as pyogenic bacteria, special bacteria (*Mycobacterium tuberculosis, Corynebacterium diphtheriae*, spirochete, etc.) viruses, fungi, and they are also divided into acute and chronic respiratory infections. When nasal cavity, pharynx, and larynx are independently infected the diseases are called by their respective organ names. However, when the above organs are infected as a whole they are called as upper airway infections, and a representing example is upper airway disease. Besides, in the event of infections due to special bacteria or fungi, they are also frequently called as upper airway tuberculosis, upper airway diphtheriae, upper airway candida and the like.

As stated above, respiratory diseases such as asthma, allergic rhinitis, acute and chronic bronchitis differ with respect to their causes and symptoms but they have common characteristics in the following few aspects.

First, they are all inflammatory diseases. These respiratory diseases are caused by allergies, infections, etc., but inflammation plays a crucial role in exacerbation and treatment of the diseases. That is, introduction of leukocytes stimulated by allergies, infections, etc., into a respiratory tract and activation therein and the various cytokines released from leukocytes and inflammatory mediators deteriorate diseases and affect the therapeutic treatment.

Second, contraction and relaxation of the respiratory tract does not perform normally thus making respiration difficult. That is, the respiratory tract is impaired thereby performing an excess reaction (asthma) in response to a normal stimulus or it becomes too narrowed to perform a normal bronchial respiration thus requiring an appropriate treatment.

Third, in major drug therapies, anti-inflammatory agents, agents that inhibit respiratory contraction, bronchodilators, agents that inhibit respiratory release play important roles and other therapeutic drugs are also commonly used in combination. For example, anti-histamine drugs, anti-cholinergic drugs, beta 2 receptor agonist, steroids, leukotriene D4 receptor antagonists, phosphodiesterase 4 inhibitor of theophyllines are commonly used. Nevertheless, bronchodilator drugs such as anti-cholinergic drugs, beta 2 receptor agonist, etc., are not effective in treating inflammation but they simply alleviate the symptoms. Therefore, long-term use of the drugs may cause drug resistance and there is also a risk of exacerbation. Steroids which are known effective in treating inflammation but they have serious side effects and are not suitable for long term use and also shown not effective in treating chronic bronchitis. Therefore, the above two drugs have been prescribed to be combined for administration but the steroids drug has been formulated in an inhalation form rather than as one for oral administration due to its adverse effects thus lowering its compliance due to the difficulty in administration. Therefore, there is a need to develop a novel therapeutic drug which can resolve the above-mentioned limitations in the currently used therapeutic drugs and effectively improve the symptoms. However, as stated above, various leukocytes and various cytokines and inflammatory mediators are involved in respiratory diseases, it is difficult to treat the respiratory diseases with a single ingredient chemical and thus a natural extract having various active ingredients and mechanism may be able to serve as an effective therapeutic drug.

Further, there appear to be many causes for respiratory diseases such as asthma, bronchitis, allergic rhinitis, acute lower respiratory infections (bronchitis, bronchiolitis, etc.), acute upper respiratory infection (tonsillitis, pharyngolaryngitis) but they are treated only for temporary release, and there is usually a problem of recurrence of the diseases after treatments. Therefore, prevention and treatment of respiratory diseases has been raised as one of the most important tasks to fulfill in medical science and the development of a novel therapeutic drug for the fundamental prevention and treatment of respiratory diseases is in urgent need.

Sophorae Radix of the present invention to be used as a crude drug is a shrub with a height of 1-2 m. It has about 2-5 cylindrical roots with yellowish brown color. Its stem has a cylindrical shape, has a groove on the surface and is densely covered with short and soft hairs where the upper part of the stem is normally bent in the form of "之", a Chinese letter. Its roots, which are used as drugs after drying, have a long cylindrical shape and are a bit bent with a length of 10-25-35 cm, a diameter of 0.3-1 cm. Its surface is brown or dark brown, has vertically-formed wrinkles and lengthy lenticels with a bit of rotation. Its main place of product is Gwangseo Province in China. In oriental medicines, it has been used to treat tumors, edema, pains, jaundice, diarrhea, hemorrhoid, and the like. Its active ingredients are alkaloids such as matrine, oxymatrine, anagyrine, methylcytisine and the like and flavonoids such as sophoranone, sophoradin, sophoranochromene, sophoradochromene and the like (Chinese Medicine Encyclopedia, Jungdam Publishing, pp. 2627-2632, 1998). However, the effect of Sophorae Radix extract on respiratory diseases has not been studied yet.

SUMMARY OF THE INVENTION

The inventors of the present invention have conducted extensive efforts to develop a therapeutic drug effective in treating respiratory diseases, and as a result, have discovered that Sophorae Radix extract has excellent activities of inhibiting airway contraction, respiratory infections, 5-lipoxygenase, phosphodiesterase 4, airway hyper-responsiveness and airway remodeling; antagonistic activity against leukotriene D4; and antitussive effect. Therefore, an object of the present invention is to provide a therapeutic drug for prevention and treatment of respiratory diseases comprising Sophorae Radix extract as an active ingredient.

BRIEF DESCRIPTION OF THE DRAWINGS

The aforementioned aspects and other features of the present invention will be explained in the following description, taken in conjunction with the accompanying drawings, wherein:

FIG. 2 A-F are pictures showing the effect of the extract prepared in Preparation Example 2 (SOS) or montelukast on airway mucus expression in lung tissues of OVA-sensitized and -challenged mice;

FIG. 4 A-F are pictures showing the effect of the extract prepared in Preparation Example 2 (SOS) or montelukast on α-smooth muscle expression in lung tissues of OVA-sensitized and -challenged mice;

FIG. 6 A-F are pictures showing the effect of the extract prepared in Preparation Example 2 (SOS) or montelukast on peribronchial fibrosis in lung tissues of OVA-sensitized and -challenged mice;

DETAILED DESCRIPTION OF THE INVENTION

In one aspect, the present invention relates to Sophorae Radix extract useful for prevention and treatment of respiratory diseases. In another aspect, the present invention relates to a pharmaceutical drug comprising Sophorae Radix extract as an active ingredient which have excellent effects of inhibiting airway contraction, respiratory infections, 5-lipoxygenase activity, phosphodiesterase 4 activity, airway hyper-responsiveness, and inhibitory activity of airway remodeling; antagonistic activity against leukotriene D4; antitussive effect; therefore being useful for prevention and treatment of respiratory diseases such as asthma, acute and chronic bronchitis, allergic rhinitis, acute lower respiratory infection (bronchitis, bronchiolitis, etc.), acute upper respiratory infection (sphagitis, tonsillitis, laryngitis) and the like.

The present invention is described in further detail hereunder.

The method of preparing Sophorae Radix extract according to the present invention is as follows.

1) Crude Sophorae Radix is extracted via reflux by using about 7 to 10 times of water or an alcohol solution with reference to the weight of Sophorae Radix and then filtered. The remnant is extracted again by adding about 4 to 7 times of water or an alcohol solution with reference to the weight of the combined Sophorae Radix, followed by heating, and then filtered. Thus obtained two filtrates are combined together and filtered.

2) The filtrate obtained in the above step 1) undergoes phase separation by using an equal amount of water-saturated low grade alcohol or a nonpolar solvent and then concentrated under reduced pressure at 50-60° C.

3) The above concentrate undergoes azeotropic concentration by adding about 20 to 50 times of water with reference to the total weight of the concentrate obtained in the above step 2), is uniformly suspended with an equal amount of water and is then placed under lyophilization.

More specifically, the original crude Sophorae Radix is added with water or an alcohol solution and extracted under reflux for 2 to 5 hrs, wherein the amount of water or an alcohol solution is preferably about 7 to 10 times with reference to the weight of crude Sophorae Radix. Then, the above extract is filtered. The filtrate is then added with about 4 to 7 times of water or an alcohol solution with reference to the weight of the crude Sophorae Radix, heated, reextracted for 2-5 hrs, filtered and combined with the previously obtained filtrate thereby increasing the extraction efficiency.

Here, if the amount of water is too little it cannot provide efficient stirring and also lower the solubility of the resulting extract thus decreasing the extraction efficiency, whereas if the amount of water is in excess it will increase the amount of low grade alcohol and the nonpolar solvent to be used in the following purification step thus being uneconomical and also raises a handling problem.

In the present invention, the extraction consists of the first extraction and the second extraction. When a crude extract is produced in bulk it usually contains a large amount of water content due to the crude drug itself although filtration is performed efficiently. Therefore, the present invention prevents the relatively low extraction efficiency obtained by the first extraction only. In addition, a further study on the extraction efficiency by the inventors of the present invention showed about 80-90% of the total extract is obtained by the second extraction, which suggests that additional extractions of more than second extraction is not necessary and also uneconomical.

The extract obtained by the first and the second extractions as stated above is filtered, concentrated and then purified to get rid of unnecessary impurities such as proteins, polysaccharides, fatty acids and the like. In the present invention, the filtrate is added with an equal amount of low grade alcohol or a nonpolar solvent to perform phase separation 2-4 times thereby obtaining solvent fraction while separating impurities. Here, examples of low grade alcohols include alcohol having carbon atoms of from 1 to 6, preferably butyl alcohol, propyl alcohol, or isopropyl alcohol. Examples of nonpolar solvents are ethylacetate, dichloromethane, chloroform, carbon tetrachloride or methylethylketone. When the amount of the low grade alcohol or the nonpolar solvent is less than that of the filtrate it often produces granules due to the presence of impurities such as fatty acids and thus the phase separation cannot be performed effectively and also the extraction efficiency on the active ingredients becomes relatively low thus being not efficient. The fraction of a low grade alcohol or a nonpolar solvent obtained as a result of the above phase separation is concentrated under reduced pressure at 50-60° C. to remove the solvent remaining in the specimen. Thus obtained concentrate undergoes azeotropic concentration 2-3 times with about 25-50 times of water with reference to the total weight of the concentrate, and then uniformly suspended by adding an equal amount of water. The main reason of performing azeotropic concentration is to effectively control the content of the remaining low grade alcohol in order to use the extract of the crude drug as a raw material for a pharmaceutical drug.

Further, the extract of Sophorae Radix of the present invention can be obtained, in addition to the above-mentioned method, by extracting with water, water-saturated low grade alcohol or a nonpolar solvent followed by purification. Examples of low grade alcohols include alcohol having carbon atoms of from 1 to 6, preferably butyl alcohol, propyl alcohol, or isopropyl alcohol. Examples of nonpolar solvents are ethylacetate, dichloromethane, chloroform, carbon tetrachloride or methylethylketone.

Thus obtained Sophorae Radix extract undergoes lyophilization and then final extract is obtained in powder form. This final extract has excellent activities of inhibiting airway contraction, respiratory inflammation, 5-lipoxygenase activity, phosphodiesterase 4 activity, airway hyper-responsiveness and airway remodeling; antagonistic activity against leukotriene D4, antitussive effect, etc., and is thus expected to be useful for the prevention and treatment of respiratory diseases.

The Sophorae Radix extract of the present invention can be administered in various oral and parenteral forms during clinical studies. When they are formulated diluents such as a filler, a bulking agent, a binder, a wetting agent, a disintegrating agent, a surfactant and the like or an excipient are used.

Solid preparations for oral administration include tablets, pills, powders, granules, capsules, troches, suppositories and the like. These solid preparations are prepared by adding at least one excipient selected from the group consisting of starch, calcium carbonate, sucrose or lactose, gelatin, and the like to a mixture of lignan and lactone compound or its derivative. Besides, in addition to a simple excipient, a lubricant such as magnesium stearate, talc, and the like can be used. Bases for suppositories are hard fat triglyceride esters, polyethylene glycol, polysorbate, cacao oil, laurin butter, glycerol, gelatin and the like.

Liquid preparations for oral administration are suspensions, solutions (syrups, drinks, etc.), emulsion and the like. For example, various excipients such as wetting agents, sweeteners, flavoring agents, and preservatives can be used in addition to the most frequently used diluents such as water and liquid paraffin.

Preparations for parenteral administration are sterilized solutions, non-aqueous solutions, suspensions, emulsions, lyophilizers. Solvents for non-aqueous solutions, suspensions or emulsions are vegetable oils, propylene glycol, polyethylene glycol, olive oil, and ethyl oleate.

Sophorae Radix extract of the present invention has been used in folk remedies for long time and its safety has been confirmed by toxicity test. The dosage of the Sophorae Radix extract depends on various factors such as the rate of body absorption, body weight, age, sex, health conditions, diets of a subject and time required for administration, method of administration, excretion rate, seriousness of diseases, and the like. As shown in pharmacological experiments, it is preferable to administer Sophorae Radix extract about 1-15 mg/kg of body weight. Therefore, the Sophorae Radix extract of the present invention to be used as an active ingredient of a pharmaceutical drug should be manufactured considering the effective range of pharmaceutical efficacies, and thus manufactured pharmaceutical preparations in the form of unit formulation can be administered at regular intervals and/or according to a specialized medication committed under the supervision of a medical specialist or by the request of a subject.

The present invention will be described in more detail with reference to the following examples, however, they should not be construed as limiting the scope of the present invention.

PREPARATION EXAMPLE 1

Preparation of Sophorae Radix Extract 250 g of Sophorae Radix minced to a size of about 1.0 cm were well mixed and added with 2 L of water and then heat-extracted for 5 hrs while stirring. The resulting filtrate was collected and the remnant was added with 1.5 L of water and heat-extracted for 3 hrs. The above two filtrates were combined and then concentrated to the final volume of 1.5 L. The above concentrate was added with an equal volume of water-saturated n-butyl alcohol and performed phase separation 3 times. Only n-butyl alcohol fraction was collected and concentrated under reduced pressure at 58° C. until the extract becomes dry. After most of the n-butyl alcohol and water are evaporated, it was added with 0.1 L of water and performed azeotropic concentration 3 times. The resultant was resuspended in an equal volume of distilled water and then lyophilized to finally obtain Sophorae Radix extract in powder.

PREPARATION EXAMPLE 2

Preparation of Sophorae Radix Extract

Sophorae Radix was cleaned with water and dried. 250 g of the Sophorae Radix was added with 2 L of 50% (v/v) ethanol solution and extracted under reflux for 6 hrs while stirring. The resulting filtrate was collected and the remnant was added with 1.5 L of 30% (v/v) ethanol solution and heat-extracted for 3 hrs. The above two filtrates were combined and then concentrated to the final volume of 1.5 L. The above concentrate was added with an equal volume of water-saturated n-butyl alcohol and performed phase separation 3 times. Only n-butyl alcohol fraction was collected and concentrated under reduced pressure at 58° C. until the extract becomes dry. After most of the n-butyl alcohol and water are evaporated, it was added with 0.2 L of water and performed azeotropic concentration 3 times. The resultant was resuspended in an equal volume of distilled water and then lyophilized to finally obtain Sophorae Radix extract in powder.

PREPARATION EXAMPLE 3

Preparation of Sophorae Radix Extract

Sophorae Radix was cleaned with water and dried. 250 g of the Sophorae Radix was added with 2 L of water-saturated butyl alcohol solution and extracted under reflux for 6 hrs while stirring. The resulting filtrate was collected and the remnant was added with 1.5 L of water-saturated butyl alcohol solution and heat-extracted for 3 hrs. The above two filtrates were combined and then concentrated under reduced pressure at 58° C. until the extract becomes dry. After most of the n-butyl alcohol and water are evaporated, it was added with 0.2 L of water and performed azeotropic concentration 3 times. The resultant was resuspended in an equal volume of distilled water and then lyophilized to finally obtain Sophorae Radix extract in powder.

EXAMPLE 1

Experiment on Inhibition of Airway Contraction (In Vitro)

To evaluate the inhibitory effect of Sophorae Radix extract prepared in Preparation Examples 1-3 against airway contraction, experiments were performed using ablated bronchi as described below and the results are shown in Table 1.
[Method]
A Hartely male guinea pig (400-450 g, SLC, Japan) was sensitized by intravenously injecting 1.5 mL/kg of anti-ovalbumin anti-serum. 48 hrs after the sensitization, the guinea pig was killed by exsanguinations and then its trachea were isolated. Other tissues attached to the bronchi were removed in Krebs-Heseleit solution and the bronchi were cut out in the form of a ring so that it contains 2-3 cartilages. While maintaining bronchial muscles intact, the cartilage parts of the ring were cut out and connected with thread on both sides and hung in an organ bath. After stabilization, it was added to induce a maximum contraction by adding 10 µg/mL of carbachol. The bronchi were washed with Krebs-Heseleit solution and stabilized. Indomethacin (2 μmoles) was added and the test material 'X' was added into organ bath one minute later. In 5 min, 10 μg/mL ovalbumin (OVA) was added to induce contraction. Rate of airway contraction was calculated by comparing contractions induced by carbachol and OVA. The airway contraction/relaxation was measured by using a physiological activity measuring device (MP150, BioPAC system) connected to a force transducer (FT4, BioPAC system).

TABLE 1

| Classification | Concentration | Inhibition Rate of Bronchial Contraction (%) |
|---|---|---|
| Preparation Example 1 | 0.25 mg/mL | 42.4 |
| | 0.5 mg/mL | 76.8 |
| Preparation Example 2 | 0.25 mg/mL | 48.8 |
| | 0.5 mg/mL | 83.0 |
| Preparation Example 3 | 0.25 mg/mL | 43.8 |
| | 0.5 mg/mL | 80.6 |
| Positive Control Montelukast | 10 μM | 24 |

As shown in the above Table 1, it was confirmed that the Sophorae Radix extract of the present invention has an effect of inhibiting airway contraction.

EXAMPLE 2

Experiment on Inhibition of Airway Contraction (In Vivo)

To evaluate the inhibitory effect of Sophorae Radix extract prepared in Preparation Examples 1-3 against airway contraction, experiments were performed as described below by exposing antigens to a sensitized guinea pig and the results are shown in Table 2.
[Method]
A Hartely male guinea pig (400-450 g, SLC, Japan) was sensitized by intravenously injecting 1.5 mL/kg of anti-ovalbumin anti-serum. 48 hrs after the sensitization, the guinea pig was administered with a drug orally. In 30 min, the guinea pig was pretreated by injecting 10 mg/kg of pyrilamine maleate, 10 mg/kg of indomethacin, and 0.1 mg/kg of propranolol subcutaneously, respectively. Then, the guinea pig was placed in Double Chamber Plethysmograph Box (HSE, Germany) installed with plethysmometer for measuring various respiratory indices and measured basic airway resistance values. 30 min after the pretreatment, 1% OVA was nebulized for 2 min in the form of aerosol by preparing a compressed air under high pressure. Airway resistance was measured for 30 min as an indicator of bronchospasm.

TABLE 2

| Classification | Amount (mg/kg) | Inhibition Rate of Bronchospasm (%) |
|---|---|---|
| Preparation Example 1 | 100 | 30 |
| | 200 | 52 |
| | 400 | 75 |
| Preparation Example 2 | 100 | 40 |
| | 200 | 55 |
| | 400 | 70 |
| Preparation Example 3 | 100 | 35 |
| | 200 | 53 |
| | 400 | 71 |
| Positive Control Montelukast | 10 | 45 |
| | 40 | 75 |

As shown in the above Table 2, it was confirmed that the Sophorae Radix extract of the present invention has an effect of inhibiting airway contraction in a sensitized guinea pig.

EXAMPLE 3

Experiment on Inhibition of Airway Infection

To evaluate the inhibitory effect of Sophorae Radix extract prepared in Preparation Examples 1-3 against bronchial inflammation, experiments were performed as described below by utilizing the increase in leukocytes such as eosinophils to the area of pulmonary bronchi by exposing antigens to a sensitized mouse and the results are shown in Table 3.
[Method]
A 6 week old BALB/c female mouse (SLC, Japan) was sensitized by administering 0.2 mL of a mixture consisting of 10 μg of OVA and alum intraperitoneally at Days 0, 7 and 14, respectively. 8 and 10 days after the last sensitization, 0.7% OVA was sprayed to the mouse for 50 min in the form of aerosol by a compressed air under high pressure to induce airway inflammation. 24 hrs after the induction of the airway inflammation, the bronchioalveolar were washed with 1.5 mL of a phosphate buffer solution. The washed solution was collected and the number of leukocytes and eosinophils in the washed solution were counted, respectively. Further, white blood cell infiltration into tissues, tissue impairments, etc., was observed by means of hematoxylin and eosin staining in the lung tissues and they were scaled accordingly. Sophorae Radix extract was orally administered 7-10 days after the last sensitization.

TABLE 3

| Classification | Amount (mg/kg) | Inhibition Rate of Airway Infection (%) |
|---|---|---|
| Preparation Example 1 | 200 | 25 |
| | 400 | 55 |
| Preparation Example 2 | 200 | 30 |
| | 400 | 50 |
| Preparation Example 3 | 200 | 28 |
| | 400 | 54 |
| Positive Control Montelukast | 10 | 24 |
| | 40 | 25 |

As shown in the above Table 3, it was confirmed that the Sophorae Radix extract of the present invention has an effect of inhibiting airway infection. While the effect of montelukast as a positive control exhibits saturation of pharmaceutical efficacy at a relatively low level without dosage-dependent effect, the Sophorae Radix extract of the present invention is shown to have sufficient pharmaceutical effect which is also dosage-dependent.

EXAMPLE 4

Inhibition of 5-Lipoxygenase (5-Lipoxygenase, 5-LO) Activity

To evaluate the inhibitory effect of Sophorae Radix extract prepared in Preparation Examples 1-3 against a leukotriene-producing enzyme, a major cause of asthma, experiments were performed as described below and the results are shown in Table 4.
[Method]
Human peripheral blood mononuclear leukocyte (PBML) was stabilized in Hank's balanced salt solution (HBSS) at 37° C. and then added with Sophorae Radix extract and allowed to react for 15 min. To the above mixture, arachidonic acid was added as a base material and produced leukotriene B4 (LTB4) for 15 min. The amount of thus produced LTB4 was measured by using Enzyme immuno assay (EIS) kit.

TABLE 4

| Classification | Concentration (mg/mL) | Inhibition Rate of 5-Lipoxygenase Activity (%) |
|---|---|---|
| Preparation Example 1 | 0.03 | 97 |
|  | 0.1 | 100 |
| Preparation Example 2 | 0.03 | 98 |
|  | 0.1 | 100 |
| Preparation Example 3 | 0.03 | 98 |
|  | 0.1 | 100 |

* positive control NDGA(Nordihydro-guaiaretic acid) $IC_{50}$ = 87.4 nM

As shown in the above Table 4, it was confirmed that the Sophorae Radix extract of the present invention has an effect of inhibiting 5-lipoxygenase activity.

EXAMPLE 5

Inhibition of Phosphodiesterase 4 (PDE4) Activity

To evaluate the inhibitory effect of Sophorae Radix extract prepared in Preparation Examples 1-3 against a phosphoesterase 4, a major cause of asthma, experiments were performed as described below and the results are shown in Table 5.

[Method]

Human U937 cells were stabilized in the mixed solution comprising 50 mM Tris-HCl and 5 mM $MgCl_2$ (pH 7.5) at 25° C. Sophorae Radix extract and 1.01 µM of ([3H]cAMP+cAMP) as a base material were combined together and allowed to react for 20 min to produce adenosine. The amount of thus produced adenosine was quantitated by measuring the amount of [3H]adenosine.

TABLE 5

| Classification | Concentration (mg/mL) | Inhibition Rate of phosphoesterase 4 (%) |
|---|---|---|
| Preparation Example 1 | 0.03 | 78 |
|  | 0.1 | 100 |
| Preparation Example 2 | 0.03 | 76 |
|  | 0.1 | 100 |
| Preparation Example 3 | 0.03 | 79 |
|  | 0.1 | 100 |

* positive control IBMX(3-isobutyl-1-methylxanthine) $IC_{50}$ = 20.7 µM

As shown in the above Table 5, it was confirmed that the Sophorae Radix extract of the present invention has an effect of inhibiting phosphoesterase 4 activity.

EXAMPLE 6

Antagonistic Activity Against Leukotriene D4 Receptor (LTD4)

To evaluate the inhibitory effect of Sophorae Radix extract prepared in Preparation Examples 1-3 against a LTD4 receptor, a major cause of asthma, experiments were performed as described below and the results are shown in Table 5.

[Method]

LTD4 receptor isolated from the pulmonary tissues of a Duncan Hartely guinea pig was stabilized in 50 mM Tris-HCl buffer solution (5 mM $CaCl_2$, 5 mM $MgCl_2$, 100 µg/mL bacitracin, 1 mM benzamidine, 0.1 mM phenylmethylsulfonyl fluoride) at 25° C. Then, Sophorae Radix extract and 0.2 nM [3H]LTD4 were added to the above mixture and allowed to react. Binding rate was analyzed via Radioligand binding assay, and non-specific binding was determined by means of 0.1 µM LTD4. Specific binding rate 85%, Kd 0.2 nM, Bmax 0.24 pmol/mg protein.

TABLE 6

| Classification | Concentration (mg/mL) | Inhibition Rate of LTD4 Receptor (%) |
|---|---|---|
| Preparation Example 1 | 0.03 | 78 |
|  | 0.1 | 89 |
| Preparation Example 2 | 0.03 | 81 |
|  | 0.1 | 89 |
| Preparation Example 3 | 0.03 | 82 |
|  | 0.1 | 88 |

* positive control LTD4 $IC_{50}$ = 1.12 nM

As shown in the above Table 6, it was confirmed that the Sophorae Radix extract of the present invention has an effect of inhibiting LTD4 receptor activity.

EXAMPLE 7

Antitussive Effect

The method used was the method by M. H. Boskabady et al. (Journal of Entnopharmacology 97, 2005, 79-82) with a bit of modifications.

A Hartley male guinea pig (450~500 g, SLC, Japan) was orally administered with a drug. 1 hr after the administration, the guinea pig was placed in Double Chamber Plethysmograph Box (HSE, Germany) installed with plethysmometer and stabilized by allowing a 5 min of time for adaptation. After the stabilization, 0.6M citric acid was sprayed to the guinea pig for 7 min in the form of aerosol by preparing a compressed air under high pressure. The guinea pig was observed continuously by a trained observer and the number of coughs induced by the above spray of citric acid aerosol was measured by using a microphone and a speaker. The coughs were distinguished from a normal sneeze due to its particular signs such as a peculiar and high sound with its mouth open, movement of abdomen, and an instant change in air flow.

TABLE 7

| Drug | Dose (mg/kg) | Cough | Inhibition (%) |
|---|---|---|---|
| CMC | 1 | 12.3 ± 2.6 (N = 7) |  |
| Preparation Example 1 | 400 | 7.8 ± 3.7 (N = 5) | 37 |
| Preparation Example 2 | 200 | 10.6 ± 2.6 (N = 8) | 14 |
|  | 400 | 6.6 ± 1.4 (N = 9) | 47 |
|  | 400 (2 h) | 8.7 ± 2.3 (N = 6) | 29 |
| Preparation Example 3 | 400 | 8.4 + 1.5 (N = 5) | 32 |
| Montelukast | 10 | 11.1 ± 2.9 (N = 9) | 10 |
|  | 40 | 11.4 ± 4.3 (N = 7) | 7 |
| Dextromethorphan | 50 | 11.1 ± 2.5 (N = 7) | 9 |
|  | 100 | 4.5 ± 2.6 (N = 10) | 63 |

As shown in the above Table 7, it was confirmed that the Sophorae Radix extract of the present invention has an antitussive effect.

EXAMPLE 8

Inhibition of Airway Hyper-Responsiveness

Figure 1:
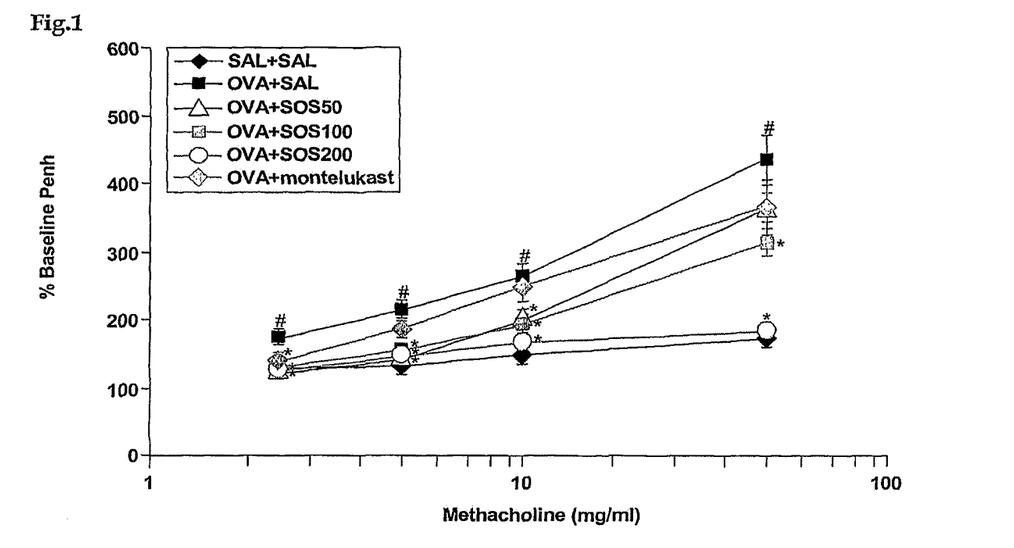
FIG. 1 is a graph showing the effect on the airway hyper-responsiveness [SAL: saline, OVA: ovalbumin, SOS: extract prepared in Preparation Example 2]

Six week old female BALB/c mice (SLC, Japan) were sensitized by administering 0.2 mL of a mixture consisting of 10 μg of OVA and alum intraperitoneally at Days 0, 7 and 14, respectively. At 8 and 10 days after the sensitization, respectively, 0.7% OVA was sprayed to the mice for 50 min in the form of aerosol by preparing a compressed air under high pressure to induce airway hyper-responsiveness. The measurement of airway hyper-responsiveness was conducted in a barometric plethysmographic chamber (All Medicus, Seoul, Korea) while allowing all the mice in the chamber free movements and with consciousness. The base value for airway hyper-responsiveness used was the average value of measurements for 3 min. Then, the mice were inhaled of methacholine for 3 min at each concentration of methacholine while gradually increasing its concentration from 2.5 mg/mL to 50 mg/mL and measured the level of airway hyper-responsiveness at each concentration, respectively. Enhanced pause (Penh) is known as a good index showing the level of airway resistance and it is calculated based on the following equation 1.

$$\text{Enhanced pause(Penh)} = [\text{expiratory time(Te)/relaxation time(RT)} - 1] \times [\text{peak expiratory flow(PEF)/peak inspiratory flow(PIF)}] \quad [\text{Equation 1}]$$

During the measurement of airway resistance, the average value of Penh is recorded every 10 sec and it is also indicated in Figures every 1 min.

As shown in the FIG. 1, it was confirmed that the Sophorae Radix extract of the present invention has an inhibitory activity against airway hyper-responsiveness.

EXAMPLE 9

Inhibition of Airway Remodeling

Eight to ten week old aseptically treated female BALB/c mice were sensitized by intraperitoneally injecting at Day 1 a mixed solution consisting of 500 μg of OVA and 1.0 mg of aluminum hydroxide (first treatment), and then inhaled with 2% OVA at Day 11 using an ultrasonic sprayer (second treatment), and finally inhaled with 3% OVA at Days 21, 22 and 23 (third treatment). The mice were then allowed to inhale 1% OVA for the following 6 weeks at intervals of 3 days and constructed an asthma model with induced airway remodeling. In the evening 24 hr prior to the 3rd OVA inhalation, the mice were administered once with the extract (SOS) prepared in Preparation Example 2. The mice were administered twice daily with the extract (SOS) prepared in Preparation Example 2 at the $3^{rd}$ OVA inhalation day (Day 21, 22, and 23), i.e., one administration at 1 hr prior to the inhalation and the other administration in the evening of the $3^{rd}$ OVA inhalation day. During the 8-week OVA inhalation period for airway remodeling, the mice were administered twice daily. The following assays were used for the analysis of the airway remodeling.

Collagen assay: Method for quantitative analysis of the level of tissue fibrosis PAS staining: Method for measurement of Goblet cell hyperplasia Peribronchial trichrome stain: Method of identifying the level of fibrosis at the lower bronchus of peribronchial area by staining tissues using Masson's trichrome. All bronchi are similar in size based on the length of the basal membrane and thus 10 bronchi with circular shape are selected and their average value is obtained. The thickness of basal membrane based on bronchioles having an internal diameter of 150-200 μm are indicated in μm and the ratio is measured by using a computerized image analyzer program.

In addition, collected lung tissues are fixed using 10% formaldehyde solution and buried in paraffin blocks. The paraffin blocks were cut into pieces with a thickness of 1.5 μm to prepare slides. Thus prepared slides were used for observation of histological changes in lungs by H&E staining.

Figure 2:
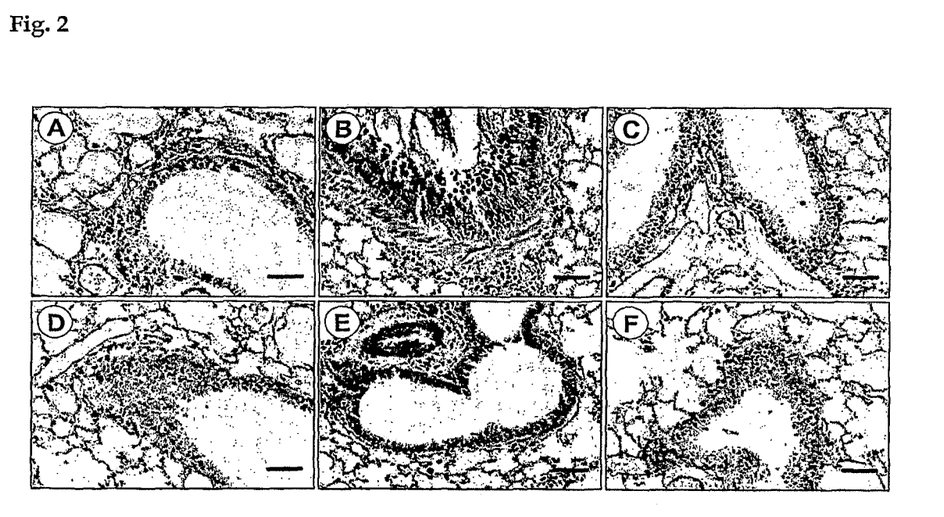

FIG. 2 shows the effect of the extract prepared in Preparation Example 2 (SOS) or montelukast on airway mucus expression in lung tissues of OVA-sensitized and -challenged mice. Representative PAS-stained sections of the lungs. Sampling was performed at 48 hrs after the last challenge in saline-inhaled mice with the administration of saline (A), OVA-inhaled mice with the administration of saline (B), OVA-inhaled mice with the administration of montelukast (C), OVA-inhaled mice with the administration of SOS 50 mg/kg (D), OVA-inhaled mice with the administration of SOS 100 mg/kg (E), and OVA-inhaled mice with the administration of SOS 200 mg/kg (F). Bars indicate scale of 50 μm. Bars indicate scale of 50 μm.

Figure 3:
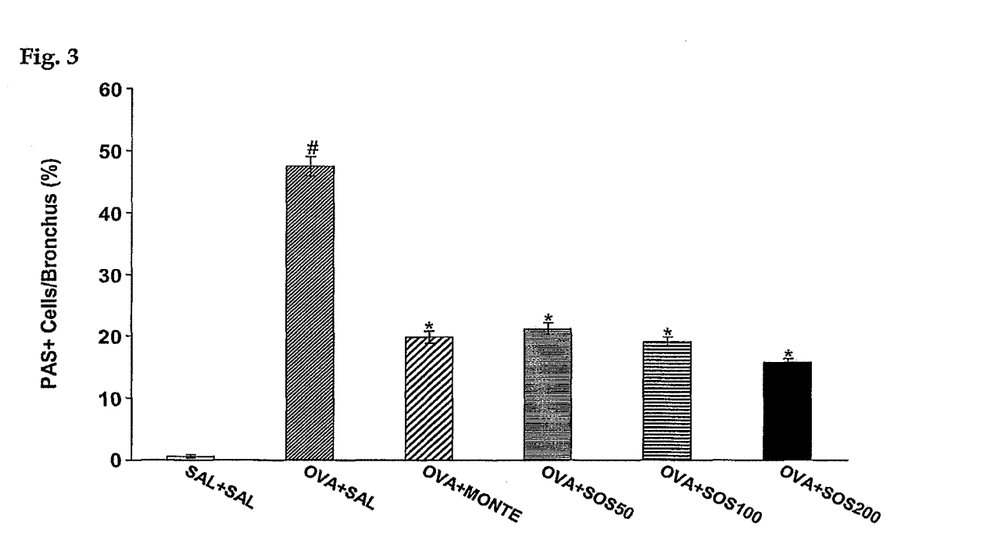
FIG. 3 is a histogram showing the effect of the extract prepared in Preparation Example 2 (SOS) or montelukast on airway mucus expression in lung tissues of OVA-sensitized and -challenged mice.

FIG. 3 is a histogram showing the effect of the extract prepared in Preparation Example 2 (SOS) or montelukast on airway mucus expression in lung tissues of OVA-sensitized and -challenged mice. The number of PAS-positive and PAS-negative epithelial cells in individual bronchioles were counted at 48 hrs after the last challenge in saline-inhaled mice with the administration of saline (SAL+SAL), OVA-inhaled mice with the administration of saline (OVA+SAL), OVA-inhaled mice with the administration of montelukast (OVA+MONTE), OVA-inhaled mice with the administration of SOS 50 mg/kg (OVA+SOS50), OVA-inhaled mice with the administration of SOS100 mg/kg (OVA+SOS100), and OVA-inhaled mice with the administration of SOS 200 mg/kg (OVA+SOS200). Bars represent the means SEM from 6 independent experiments. #, $p < 0.05$ versus SAL+SAL; *, $p < 0.05$ versus OVA+SAL.

The percentage of airway epithelium staining positively with PAS was increased significantly at 48 hrs after OVA inhalation compared to the percentage after saline inhalation (FIGS. 2 and 3). The increased percentage of airway epithelium staining positively with PAS was significantly reduced by the administration of SOS or montelukast.

Figure 4:
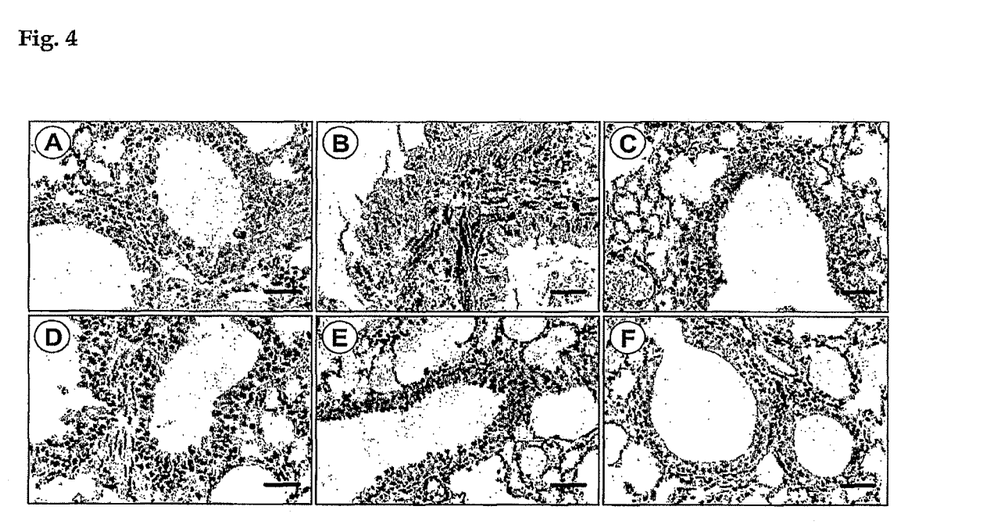

FIG. 4 shows the effect of the extract prepared in Preparation Example 2 (SOS) or montelukast on α-smooth muscle expression in lung tissues of OVA-sensitized and -challenged mice. Representative immunohistochemical-stained sections for α-smooth muscle actin of the lungs. Sampling was performed at 48 hrs after the last challenge in saline-inhaled mice with the administration of saline (A), OVA-inhaled mice with the administration of saline (B), OVA-inhaled mice with the administration of montelukast (C), OVA-inhaled mice with the administration of SOS 50 mg/kg (D), OVA-inhaled mice with the administration of SOS 100 mg/kg (E), and OVA-inhaled mice with the administration of SOS 200 mg/kg (F). Bars indicate scale of 50 μm. Bars indicate scale of 50 μm.

Figure 5:
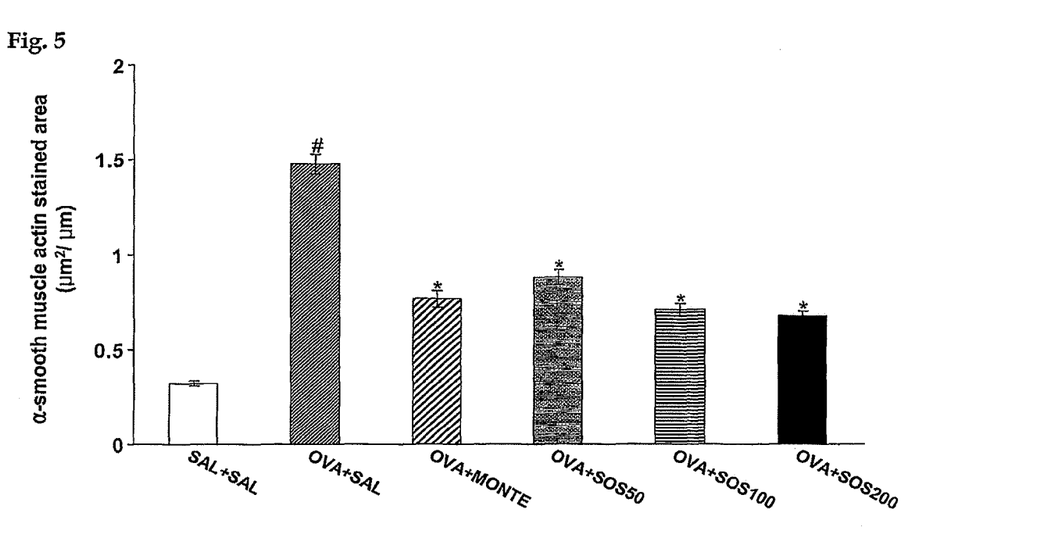
FIG. 5 is a histogram showing the effect of the extract prepared in Preparation Example 2 (SOS) or montelukast on α-smooth muscle expression in lung tissues of OVA-sensitized and -challenged mice.

FIG. 5 shows the effect of the extract prepared in Preparation Example 2 (SOS) or montelukast on α-smooth muscle expression in lung tissues of OVA-sensitized and -challenged mice. The area of immunostaining of α-smooth muscle actin was measured at 48 hrs after the last challenge in saline-inhaled mice with the administration of saline (SAL+SAL), OVA-inhaled mice with the administration of saline (OVA+SAL), OVA-inhaled mice with the administration of montelukast (OVA+MONTE), OVA-inhaled mice with the administration of SOS 50 mg/kg (OVA+SOS50), OVA-inhaled mice with the administration of SOS100 mg/kg (OVA+SOS100), and OVA-inhaled mice with the administration of SOS 200 mg/kg (OVA+SOS200). Bars represent the means SEM from 6 independent experiments. #, p<0.05 versus SAL+SAL; *, p<0.05 versus OVA+SAL.

The area of peribronchial α-smooth muscle actin immunostaining was increased significantly at 48 hrs after OVA inhalation compared to the area after saline inhalation (FIGS. 4 and 5). The increased area of peribronchial α-smooth muscle actin immunostaining was significantly reduced by the administration of SOS or montelukast.

Figure 6:
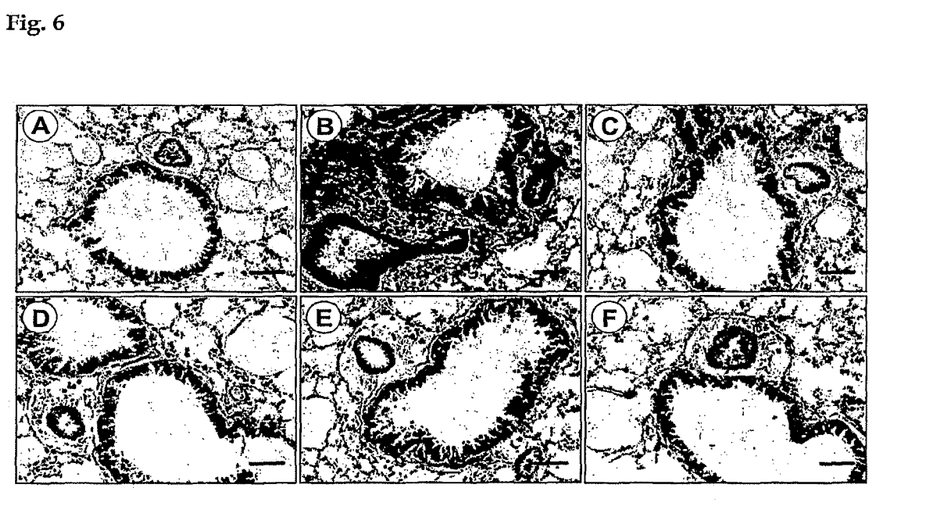

FIG. 6 shows the effect of the extract prepared in Preparation Example 2 (SOS) or montelukast on peribronchial fibrosis in lung tissues of OVA-sensitized and -challenged mice. Representative Masson Trichrome-stained sections of the lungs. Sampling was performed at 48 hrs after the last challenge in saline-inhaled mice with the administration of saline (A), OVA-inhaled mice with the administration of saline (B), OVA-inhaled mice with the administration of montelukast (C), OVA-inhaled mice with the administration of SOS 50 mg/kg (D), OVA-inhaled mice with the administration of SOS100 mg/kg (E), and OVA-inhaled mice with the administration of SOS 200 mg/kg (F). Bars indicate scale of 50 μm.

Figure 7:
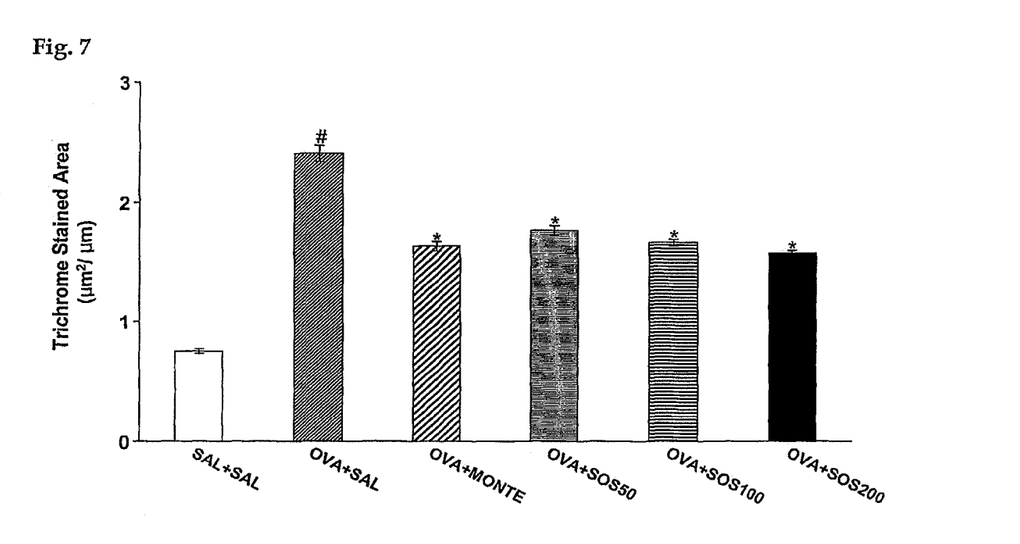
FIG. 7 is a histogram showing the effect of the extract prepared in Preparation Example 2 (SOS) or montelukast on fibrosis in lung tissues of OVA-sensitized and -challenged mice.

FIG. 7 shows the effect of the extract prepared in Preparation Example 2 (SOS) or montelukast on fibrosis in lung tissues of OVA-sensitized and -challenged mice. The area of peribronchial trichrome staining in paraffin-embedded lung was measured at 48 hrs after the last challenge in saline-inhaled mice with the administration of saline (SAL+SAL), OVA-inhaled mice with the administration of saline (OVA+SAL), OVA-inhaled mice with the administration of montelukast (OVA+MONTE), OVA-inhaled mice with the administration of SOS 50 mg/kg (OVA+SOS50), OVA-inhaled mice with the administration of SOS100 mg/kg (OVA+SOS100), and OVA-inhaled mice with the administration of SOS 200 mg/kg (OVA+SOS200). Bars represent mean SEM from 6 independent experiments. Bars represent the means SEM from 6 independent experiments. #, p<0.05 versus SAL+SAL; *, p<0.05 versus OVA+SAL.

The area of peribronchial trichrome staining was increased significantly at 48 hrs after OVA inhalation compared to the area after saline inhalation (FIGS. 6 and 7). The increased area of peribronchial trichrome staining was significantly reduced by the administration of SOS or montelukast.

Figure 8:
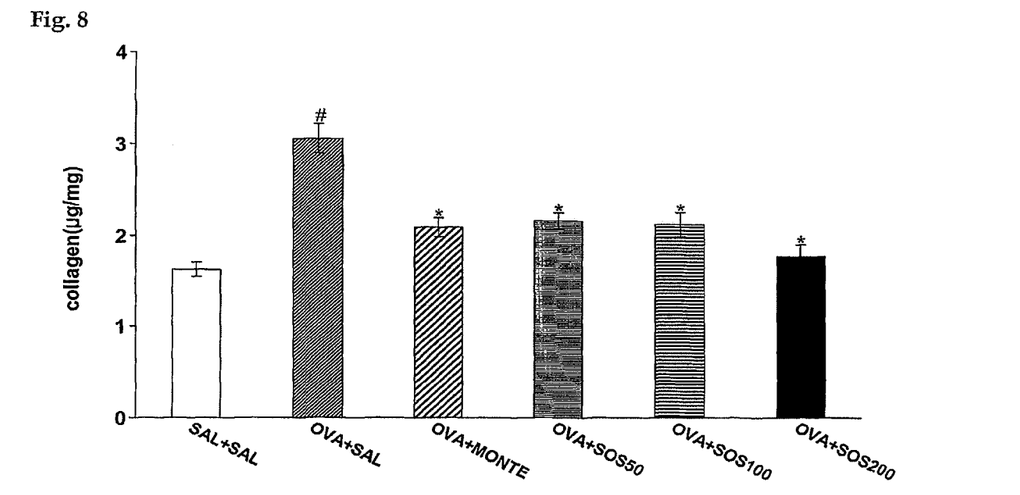
FIG. 8 is a histogram showing the effect of the extract prepared in Preparation Example 2 (SOS) or montelukast on total lung collagen content of OVA-sensitized and -challenged mice.

FIG. 8 shows the effect of the extract prepared in Preparation Example 2 (SOS) or montelukast on total lung collagen content of OVA-sensitized and -challenged mice. The amount of lung collagen was measured using a collagen assay kit. Sampling was performed at 48 hrs after the last challenge in saline-inhaled mice with the administration of saline (SAL+SAL), OVA-inhaled mice with the administration of saline (OVA+SAL), OVA-inhaled mice with the administration of montelukast (OVA+MONTE), OVA-inhaled mice with the administration of SOS 50 mg/kg (OVA+SOS50), OVA-inhaled mice with the administration of SOS100 mg/kg (OVA+SOS100), and OVA-inhaled mice with the administration of SOS 200 mg/kg (OVA+SOS200). Bars represent the means SEM from 6 independent experiments. #, p<0.05 versus SAL+SAL; *, p<0.05 versus OVA+SAL.

The levels of lung collagen were increased significantly at 48 hrs after OVA inhalation compared to the area after saline inhalation (FIG. 8). The increased levels of lung collagen were significantly reduced by the administration of SOS or montelukast.

EXAMPLE 10

Measurement of Cytokines (IL-4, 5 and 13) OVA-Specific IgE Via Western Blot Analysis The concentration of cytokines (IL-4, 5 and 13) in the washed solution of lung tissues and the concentration of OVA-specific IgE in the serum were measured by using ELISA kit(cytokine: R&D systems, Abingdon, UK/OVA-specific IgE; BD sciences).

Figure 9:
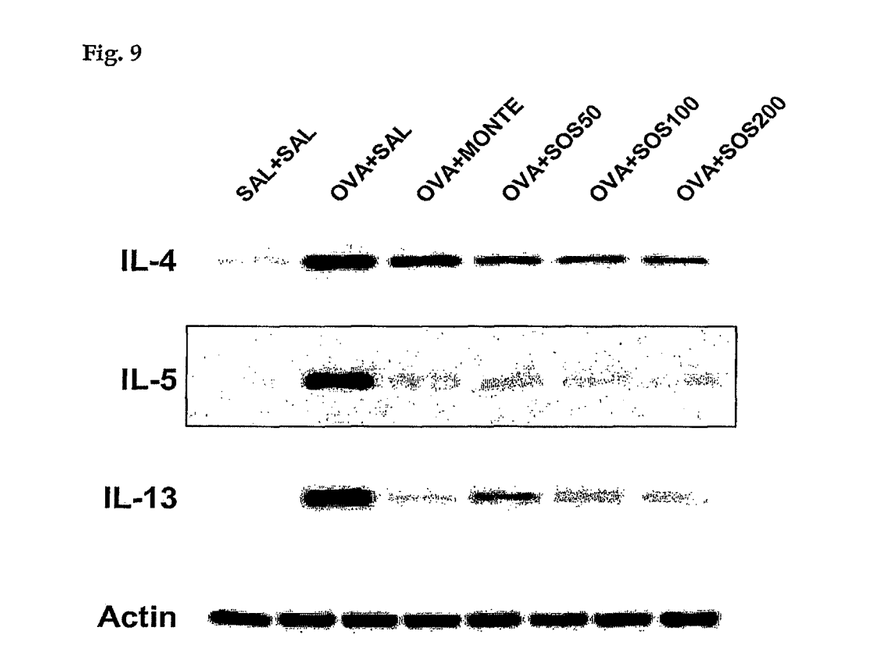
FIG. 9 is a result of Western blot showing the effect of the extract prepared in Preparation Example 2 (SOS) or montelukast on IL-4, IL-5, and IL-13 protein expression in lung tissues of OVA-sensitized and -challenged mice.

FIG. 9 shows the effect of the extract prepared in Preparation Example 2 (SOS) or montelukast on IL-4, IL-5, and IL-13 protein expression in lung tissues of OVA-sensitized and -challenged mice. IL-4, IL-5, and IL-13 protein expression were measured at 48 hrs after the last challenge in saline-inhaled mice with the administration of saline (SAL+SAL), OVA-inhaled mice with the administration of saline (OVA+SAL), OVA-inhaled mice with the administration of montelukast (OVA+MONTE), OVA-inhaled mice with the administration of SOS 50 mg/kg (OVA+SOS50), OVA-inhaled mice with the administration of SOS100 mg/kg (OVA+SOS100), and OVA-inhaled mice with the administration of SOS 200 mg/kg (OVA+SOS200). Results were similar in 8 independent experiments.

Western blot analysis revealed that levels of IL-4, IL-5, and IL-13 protein in lung tissues were increased significantly at 48 hrs after OVA inhalation compared to the levels after saline inhalation (FIG. 9). The increased levels of these cytokines were significantly reduced by the administration of SOS or montelukast.

EXAMPLE 11

Toxicity Test on Repeated Oral Administration in Rats

Toxicity tests with repetitive administration were performed using six week old specific pathogen free (SPF) SD rats as follows.

Sophorae Radix extract prepared in Preparation Examples 1-3 were suspended and administered orally in the amount of 2 g/kg for a period of 2 weeks to rats. Each group contained six animals.

After the administration, the mice were observed with respect to their death, clinical symptoms, change in body weight, hematological and hematobiochemical tests were performed. The mice were then autopsied to examine any abnormalities in their abdominal and pectoral organs with naked eyes. The results showed that all the mice survived and there were no particular signs in terms of clinical symptoms. Further, there were no significant findings in toxicity test in hematological and hematobiochemical tests as well as in autopsies.

Therefore, it was confirmed that the Sophorae Radix extract of the present invention is a safe material which does not exhibit any toxicity in rats up to the dosage of 2,000 mg/kg.

FORMULATION EXAMPLE 1

Preparation of Tablets

Sophorae Radix extract of the present invention with the following composition was formulated in tablets for oral administration by using wet granulation and dry granulation methods.

[Composition]

Sophorae Radix extract 250 mg, light anhydrous silicone dioxide 10 mg, magnesium stearate 2 mg, microcrystalline cellulose 50 mg, sodium starch glycolate 25 mg, corn starch 113 mg, adequate amount of anhydrous ethanol.

FORMULATION EXAMPLE 2

Preparation of Ointments

Sophorae Radix extract of the present invention with the following composition was formulated in ointments.
[Composition]
Sophorae Radix extract 7 g, cetyl palmitate 20 g, cetanol 40 g, stearyl alcohol 40 g, isopropyl myristate 80 g, sorbitan monostearate 20 g, polysorbate 60 g, propyl parahydroxybenzoate 1 g, methyl parahydroxybenzoate 1 g, adequate amount of phosphate and purified water

FORMULATION EXAMPLE 3

Preparation of Injectables

Sophorae Radix extract of the present invention with the following composition was formulated in injectables.
[Composition]
Sophorae Radix extract 50 mg, mannitol 180 mg, $Na_2HPO_4$ 25 mg, injectable distilled water 2,970 mg

FORMULATION EXAMPLE 4

Preparation of Topical Agents

Sophorae Radix extract of the present invention with the following compositions was formulated in topical agents.
[Composition 1]
Sophorae Radix extract 0.3 g, sodium polyacrylate 1.3 g, glycerine 3.6 g, hydroxy aluminum 0.04 g, methyl parabene 0.2 g, water 14 g.
[Composition 2]
Sophorae Radix extract 0.6 g, propylene glycol 1.6 g, liquid paraffin 0.8 g, isopropyl myristate 0.4 g, acrylic adhesive 1430 g, water 16.4 g.

FORMULATION EXAMPLE 5

Preparation of Troches

Sophorae Radix extract of the present invention with the following composition was formulated in troches.
[Composition]
Sophorae Radix extract 1 g, white sugar 50 g, gelatin 3 g, glycerine 10 g, acacia gum 1 g, adequate amount of water

FORMULATION EXAMPLE 6

Preparation of Syrups

Sophorae Radix extract of the present invention with the following composition was formulated in syrups.
[Composition]
Sophorae Radix extract 2 g, saccharin 0.8 g, sugar 25.4 g, glycerine 8.0 g, flavor 0.04 g, ethanol 4.0 g, sorbic acid 0.4 g, adequate amount of distilled water Industrial Applicability As stated above, the Sophorae Radix extract of the present invention, unlike the conventional synthesized pharmaceutical drugs which have shown effective only in limited cases of respiratory diseases model, have exhibited excellent pharmaceutical efficacies in overall respiratory diseases model. That is, the Sophorae Radix extract of the present invention has excellent effect of inhibiting airway contraction, respiratory infections, 5-lipoxygenase activity, phosphodiesterase 4 activity, airway hyper-responsiveness and airway remodeling; antagonistic activity against leukotriene D4; and antitussive effect, thus being useful for prevention and treatment of respiratory diseases, such as asthma, acute and chronic bronchitis, allergic rhinitis, acute lower respiratory infections (bronchitis, bronchiolitis, etc.), acute upper respiratory infections (sphagitis, tonsillitis, laryngitis).

All documents mentioned herein are fully incorporated herein by reference in their entirety.

While the invention has been described with reference to specific embodiments, modifications and variations of the invention may be constructed with departing from the scope of the invention, which is defined in the following claims.

What is to be claimed is:

1. A method of treating asthma, cough, or allergic rhinitis in a patient in need thereof comprising administering to the patient an effective amount of a purified extract of Sophorae subprostratae Radix, wherein the extract is prepared by the steps of:
   (a) extracting Sophorae subprostratae Radix with an ethanol solution,
   (b) filtering the ethanol extract solution, collecting the filtrate, and concentrating the filtrate;
   (c) adding a water-saturated n-butanol solvent to the concentrated filtrate to obtain a water-saturated n-butanol solution,
   (d) subjecting the water-saturated n-butanol solution to phase separation to obtain an n-butanol fraction,
   (e) concentrating and drying the n-butanol fraction to produce the purified extract.

2. The method of claim 1, wherein the n-butanol fraction is concentrated under reduced pressure at 50-60 ° C.

3. The method of claim 2, wherein the n-butanol fraction is concentrated azeotropically.

4. The method of claim 3, wherein the purified extract is lyophilized.

5. The method of claim 1, wherein the purified extract is administered in an oral or parenteral form.

6. The method of claim 5, wherein the purified extract is administered in an oral form selected from the group consisting of: tablet, pill, powder, granule, capsule, troche, suppository, suspension, solution and emulsion.

7. The method of claim 1, wherein the purified extract is administered in a dose of about 1-15 mg/kg of body weight.

8. The method of claim 1, wherein the patient suffers from asthma.

9. The method of claim 1, wherein the patient suffers from a cough.

10. The method of claim 1, wherein the patient suffers from allergic rhinitis.

* * * * *